US012765845B2

(12) United States Patent
Purdy et al.

(10) Patent No.: US 12,765,845 B2
(45) Date of Patent: Oct. 20, 2026

(54) ORIENTATION SYSTEM FOR SPECIMEN IMAGING APPARATUS

(71) Applicant: Faxitron Bioptics, LLC, Marlborough, MA (US)

(72) Inventors: Ciaran Purdy, Wilmington, DE (US); Brad Jackson, Marlborough, MA (US); Jared Moore, Marlborough, MA (US)

(73) Assignee: Faxitron Bioptics, LLC, Marlborough, MA (US)

( * ) Notice: Subject to any disclaimer, the term of this patent is extended or adjusted under 35 U.S.C. 154(b) by 13 days.

(21) Appl. No.: 18/924,489

(22) Filed: Oct. 23, 2024

(65) Prior Publication Data

US 2025/0134477 A1 May 1, 2025

Related U.S. Application Data

(63) Continuation of application No. 17/295,501, filed as application No. PCT/US2019/062481 on Nov. 20, 2019, now Pat. No. 12,156,753.

(60) Provisional application No. 62/769,683, filed on Nov. 20, 2018.

(51) Int. Cl.

| | |
|---|---|
| ***A61B 6/03*** | (2006.01) |
| ***A61B 6/50*** | (2024.01) |
| ***A61B 90/00*** | (2016.01) |
| ***G06V 10/24*** | (2022.01) |

(52) U.S. Cl.

CPC .............. *A61B 6/032* (2013.01); *A61B 6/508* (2013.01); *A61B 90/39* (2016.02); *G06V 10/245* (2022.01)

(58) Field of Classification Search
None
See application file for complete search history.

(56) References Cited

U.S. PATENT DOCUMENTS

| | | | |
|---|---|---|---|
| 3,055,808 | A | 9/1962 | Henderson |
| D237,981 | S | 12/1975 | Mastrell |
| D322,323 | S | 12/1991 | Moir |
| 5,449,071 | A | 9/1995 | Levy |
| D439,637 | S | 3/2001 | Davies |
| D521,381 | S | 5/2006 | Hicks |
| D535,755 | S | 1/2007 | Discko, Jr. |
| D674,505 | S | 1/2013 | Cecchi |

(Continued)

FOREIGN PATENT DOCUMENTS

| | | |
|---|---|---|
| WO | 2017040977 | 3/2017 |
| WO | 2019/051496 | 3/2019 |

OTHER PUBLICATIONS

European Extended Search Report in Application 19817561.4, mailed Jun. 14, 2023, 7 pages.

(Continued)

*Primary Examiner* — Yi-Shan Yang
(74) *Attorney, Agent, or Firm* — Merchant & Gould P.C.

(57) ABSTRACT

A method of generating images of a specimen that includes triggering a source of electromagnetic radiation to emit a beam of electromagnetic radiation along an axis through a tissue specimen and towards an imaging detector, generating at least one image with the received beam at the imaging detector, and superimposing, into or adjacent the at least one image by a system controller, a set of graphical indications that convey portions of a patient's body from which respective portions of the specimen were assumed to have been excised.

20 Claims, 13 Drawing Sheets

(56) References Cited

U.S. PATENT DOCUMENTS

| | | | | |
|---|---|---|---|---|
| D781,437 | S | 3/2017 | Valley | |
| D787,053 | S | 5/2017 | Huang | |
| D804,051 | S | 11/2017 | Alexander | |
| D827,151 | S | 8/2018 | Nakagawa | |
| D895,838 | S | 9/2020 | Purdy et al. | |
| D925,759 | S | 7/2021 | Suzuki | |
| D927,015 | S | 8/2021 | Thomas | |
| D930,850 | S | 9/2021 | Zollinger | |
| D956,264 | S | 6/2022 | Purdy | |
| 12,156,753 | B2 | 12/2024 | Purdy | |
| 2005/0089997 | A1 | 4/2005 | Minton | |
| 2007/0210252 | A1 | 9/2007 | Miyamoto | |
| 2011/0103676 | A1 * | 5/2011 | Mullaney | A61B 90/36 382/132 |
| 2015/0237327 | A1 * | 8/2015 | Rustici | H04N 13/254 378/20 |
| 2016/0367992 | A1 | 12/2016 | Purdy | |
| 2017/0241897 | A1 * | 8/2017 | Berkeley | A61B 3/0025 |
| 2017/0336706 | A1 * | 11/2017 | Wang | A61B 5/0071 |
| 2018/0043365 | A1 | 2/2018 | Ruby | |

OTHER PUBLICATIONS

High-Precision Rotation Mount, Thorlabs, 3 pages (2016), retrieved from the internet: https:///web.archive.org/web/20160619045759/https://www.thorlabs.com/newgrouppage9.cfm?objectgroup_id=2464.

PCT International Preliminary Report on Patentability in International Patent Application No. PCT/US2019/062481 mailed Jun. 3, 2021, 12 pages.

PCT International Search Report and Written Opinion of the International Searching Authority for International Patent Application No. PCT/US2019/062481 mailed Feb. 21, 2020, 17 pages.

European Communication pursuant to Article 94(3) EPC in Application 19817561.4, mailed Jun. 10, 2026, 8 pages.

Barry, Kate et al., “A clinical audit of anatomical side marker use in a paediatric medical imaging department”, Journal of Medical Radiation Sciences, vol. 63, No. 3, May 25, 2016; 148-154.

* cited by examiner

ORIENTATION SYSTEM FOR SPECIMEN IMAGING APPARATUS

CROSS-REFERENCE TO RELATED APPLICATIONS

This application is a continuation of U.S. patent application Ser. No. 17/295,501, filed May 20, 2021, now U.S. Pat. No. 12,156,753, which is a National Stage Application of PCT/US2019/062481, filed Nov. 20, 2019, and claims priority to U.S. Provisional Patent Application No. 62/769,683, filed Nov. 20, 2018, the entire disclosures of which are incorporated herein by reference herein in their entireties.

FIELD OF THE INVENTION

This invention generally relates to the imaging of objects such as tissue specimens.

BACKGROUND OF THE INVENTION

There are currently numerous non-invasive imaging techniques that can be used to produce images of a given object for use in inspection, analysis, and the like. Such techniques include X-rays, magnetic resonance imaging ("MRI"), computed tomography ("CT" or "microtomography") scans, ultrasound and optical imaging using structured light, among others.

As an example, mammography is the process of using low-energy x-rays to examine the human breast for diagnosis and screening with the goal being the early detection of breast cancer. With mammography images, the orientation of the breast relative to the patient's body is easily known as radiologists use standard medical terminology to express orientation of the image. For instance, in most cases a patient will have a "Medial-Lateral" (e.g., side to side) image taken and a "Cranial-Caudal" (or Superior-Inferior) (e.g., top to bottom) image taken and the mammography software displays these orientations markers on a display in or with the images.

If characteristic masses or microcalcifications are detected in the mammography images, suspicious tissue (e.g., lesion) can be removed (e.g., biopsied) by a surgeon for further examination by a radiologist and/or pathologist. After a surgeon has appropriately identified a location of a possible lesion, the surgeon proceeds to excise tissue that includes the lesion and then verify that the entirety of the suspicious area is within the margins of the excised tissue. In this regard, a radiologist or the surgeon will x-ray the excised tissue specimen from multiple views (e.g., orthogonal views) to confirm appropriate tissue margins. Once the tissue margins have been confirmed, the surgeon may then appropriately mark or otherwise indicate where, on the excised tissue specimen, a pathologist should focus during subsequent analysis and diagnosis. If the suspicious tissue is too close or even contacts the tissue edges, the surgeon may need to excise additional tissue. Accordingly, it is important for the radiologist and surgeon to have confidence from the various images of the tissue specimen that the tissue margins are sufficient and that all potentially cancerous or worrisome tissue is fully contained within the removed tissue to limit the number of further tissue excisions.

It is important during the examination of the specimen to understand how the specimen is oriented relative to the patient's body. For instance, the radiologist can bring up the patient's mammography images as reference to see how the specimen images relate to those of the whole breast. Oftentimes, markers in the tissue can be used to position and orient the specimen image relative to the mammography image. However, doing so is often very difficult as the mammography images and specimen images are typically captured from different perspectives. Because the radiologist must be able to accurately communicate concerns in the specimen images to the surgeon for use in re-excisions, understanding how the specimen is oriented relative to the patient's body is of great importance. Accurately understanding such orientation is also important to pathologists post-surgery. After surgical excision, the specimen may be clipped or inked to indicate a specific orientation for pathology. However, such efforts are time consuming and may be only relevant to a person who is familiar with the same system of marking.

SUMMARY

Disclosed herein are apparatuses, systems, and methods ("utilities") for use in automatically graphically presenting, in or adjacent resulting images of an object such as a specimen, one or more orientation indications of the specimen relative to a patient's body for use by surgeons, radiologists, pathologists, and other medical professionals. Broadly, the disclosed utilities are configured to instruct a medical professional to position and orient a specimen in a particular manner in preparation for imaging such that the graphical orientation indications imparted into the resulting images automatically align with the respective corresponding portions of the specimen in the images. As an example, the various orientation indications may indicate a different respective portion or location in the patient's body from which the specimen was extracted. For instance, the various portions or locations may be related to a various particular standard anatomical terms of location of the patient's body such as one of cranial (superior), caudal, (inferior), medial (center), lateral (side to side), posterior (back), or anterior (front). In one arrangement, a particular portion of the specimen may be oriented on a receiving surface of a platform relative to a particular fixed portion of the system (e.g., x-ray source) in preparation for imaging and then a computing system (e.g., logic) associated with the system may be configured to automatically impart relative orientation indications into resulting images as discussed in more detail herein.

In one arrangement, the disclosed utilities may include and make use of one or more indicators that are configured to convey to an operator or technician a particular manner in which the specimen is to be oriented on a receiving surface relative to a source of electromagnetic radiation in preparation for imaging of the specimen. More particularly, the particular orientation may ensure that the orientation of the specimen in the image corresponds to the graphical indication orientations automatically imparted into the images by the system controller.

As an example, the disclosed utilities may find use in the context of an imaging system having a source of electromagnetic radiation that is configured to emit a beam of electromagnetic radiation through a specimen disposed over a receiving surface of a rotatable platform for receipt at an imaging detector. The rotatable platform may be rotatable about a rotation axis and may include a "home" position about the rotation axis that is known to a system controller that manages generation of the beam of electromagnetic radiation, receipt of the beam at the detector, generation of corresponding images, and the like. In the case of two-dimensional images of the specimen, the system may be configured to obtain one two-dimensional image of the specimen with the platform in the home position and another two-dimensional image of the specimen with the platform (and thus the specimen) being rotated 90 degrees about the rotation axis. In the case of a three-dimensional image, the system may be configured to obtain a plurality of images of the specimen as the platform (and thus the specimen) are being rotated about the rotation axis from the home position and then reconstruct the images into a three-dimensional data set and a corresponding three-dimensional image which can be manipulated by a technician or the like to analyze the tissue margins.

In either case, an operator of the system may be instructed to position the specimen over the receiving surface of the platform in its home position such that a particular portion of the specimen (e.g., a first portion of the specimen facing a first anatomical region of the patient (e.g., the caudal region) before excision) faces towards a first particular fixed portion of the system (e.g., such as the source of electromagnetic radiation). In one arrangement, the system may include one or more indicators to aid the operator in positioning the specimen such that the particular portion of the specimen faces towards the first particular fixed portion of the system. For instance, at least one indicator may be physically disposed on or projected onto a portion of the platform such that, when the operator positions the specimen over the platform with the particular portion facing, near, and/or adjacent the indicator, the particular portion of the specimen may face the first particular fixed portion of the system with the platform in its home position. Stated differently, the at least one indicator may be aligned with or face towards the first particular fixed portion of the system. The at least one indicator may be in the form of a tab, projection, print, marker, wording, radiopaque ink, light, and/or the like. In one variation, the indicator may be located on or may form part of a particular fixed portion of the platform.

In one arrangement, the operator may additionally be instructed to position another particular (e.g., anatomical) portion of the specimen (e.g., a portion of the specimen facing a second anatomical region of the patient (e.g., the anterior region) before excision) to face towards another portion of the system (e.g., such as upwardly). In any case, logic associated with the system controller can then automatically impart, based on a rotational position of platform, a particular set of orientation indications into the resulting images to indication different anatomical portions of the specimen in the image. For instance, in a "home" or first rotational position of the platform, the system controller may be configured to automatically impart into or alongside the resulting image a first set of graphical anatomical indications (e.g., anterior portion at top of image, lateral on side of image, etc.). As discussed herein, the surgeon or radiologist may be instructed (e.g., via the at least one indicator, instructions on a screen, etc.) to position the specimen over the platform in its home position in a manner such that the anterior portion of the specimen is in the top of the resulting image, the lateral portion of the specimen is on the side of the image, the caudal portion of the specimen is facing the viewer in the image, etc. Accordingly, the first set of graphical anatomical indications imparted by the controller into the image may correspond with the specimen in the manner in which it was placed by the surgeon or pathologist over the platform.

In one embodiment, the platform may include a reusable lower portion (e.g., stage) that is fixedly attached to a motion control mechanism of the system and a disposable upper portion (e.g., tray) that is removably attached to the lower portion and that is configured to (directly) receive the specimen thereon. The platform may also include any appropriate rotation prevention mechanism that inhibits relative rotation between the upper and lower portions about the rotation axis. Stated differently, the rotation prevention mechanism is configured to allow the upper and lower portions to rotate as a single unit about the rotation axis of the platform so that torque applied to the lower portion by a rotary drive of the system is automatically imparted to the upper portion.

As an example, the rotation prevention mechanism may include a first rotation prevention device (e.g., one of a male and female member) on the upper portion and a corresponding second rotation prevention device (e.g., the other of a male and female member) on the lower portion, where the first and second rotation prevention devices are engageable to prevent rotation of the upper portion relative to the lower portion about the rotation axis. In one arrangement, one of the first and second rotation prevention devices is an opening having a non-circular outer perimeter, and the other of the first and second rotation prevention devices is a member having a corresponding non-circular outer perimeter that is receivable in the opening to prevent rotation of the upper portion relative to the lower portion about the rotation axis. For instance, the first rotation prevention device may be a non-circular opening on a bottom of the upper portion of the platform and the second rotation prevention device may be a member with a non-circular outer perimeter on the lower portion of the platform. In this regard, the upper portion of the platform may be positioned over the lower portion of the platform and then rotated about the rotation axis until the non-circular member fits into the non-circular opening to thereafter prevent relative rotation between the upper and lower portions of the platform (e.g., until the upper portion is lifted off of the lower portion after an imaging procedure).

The system may also be configured vice versa whereby the lower portion has a non-circular opening and the upper portion includes a non-circular member configured for receipt in the non-circular opening. Various other arrangements for inhibiting rotation of the upper portion relative to the lower portion in one or more particular positions about the rotation axis are envisioned and encompassed herein (e.g., such as one or more asymmetrical members).

Use of a platform having separate upper and lower portions advantageously allows a surgeon or the like to initially position a specimen onto the upper receiving surface of the upper portion with the upper portion separated and remote from the lower portion. For instance, this step may be performed near the surgery site or in other words at least somewhat remote from the imaging cabinet and lower portion of the platform. After the surgeon has placed the specimen onto the receiving surface with the particular specimen portion facing the indicator (e.g., and additionally with a second particular portions of the specimen facing in another particular direction as discussed herein), the surgeon may thereafter be able to non-rotatably position the upper portion (with specimen thereon) over the lower portion of the platform such that the indicator and particular portion of the specimen are directed towards the first particular fixed portion of the system (e.g., x-ray source) in a home position of the platform. However, the surgeon or the like may also be able to position the specimen over the platform with the upper portion already non-rotatably positioned over the lower portion of the platform.

In the case of a first two-dimensional image of the specimen obtained by passing a beam of electromagnetic radiation from the source through the specimen and to the detector with the platform in its home position, the system controller may automatically display a first set of graphical anatomical indications in or along with the image (e.g., anterior portion at top of image, lateral on side of image, etc.) that correspond to a manner in which a specimen is assumed to have been oriented over the platform in its home position. As known, for instance, the anterior and posterior portions of a patient are disposed on a first anatomical axis, the cranial and caudal portions are disposed on a second anatomical axis, and first and second lateral portions are disposed on a third anatomical axis, where the first, second, and third anatomical axes are all perpendicular to each other. The system controller may use such axes to automatically impart or superimpose corresponding indications into or alongside the resulting image. For instance, the system controller may automatically impart, into the first image with the platform in its home position, corresponding anterior and posterior graphical indications near the top and bottom of the image (e.g., along one reference axis) and medial and lateral indications into the left and right sides of the image (e.g., along another reference axis)

The system may then rotate the platform (e.g., by 90 degrees or the like) from the first (home) rotational position to a second rotational position and obtain at least a second two-dimensional image and automatically impart a second set of graphical orientation indications into or alongside the second image, where the second set of graphical orientation indications correspond to an assumed orientation of the specimen relative to the beam of electromagnetic radiation after the platform has been rotated to its second rotational position. As discussed previously, the various anatomical axes are perpendicular to each other. Accordingly, assuming that the platform is rotated by 90 degrees between the first and second rotational positions, the second set of graphical orientation indications imparted into or with the second image may be 90 degrees rotated relative to the first set of graphical orientation indications. For instance, the anterior and posterior indications may still be positioned near the top and bottom of the image as the rotation axis about which the platform was rotated is parallel to the reference axis interconnecting the anterior and posterior portions. However, the cranial and caudal graphical indications may now be positioned on the sides of the image and the medial and lateral graphical indications may no longer be in the image as these portions face towards the view and away from the viewer.

The controller may automatically convey graphical orientation indications in the resulting image(s) in any appropriate manner. As one example, the controller may utilize numbers, letters, and/or words to connote the various portions of the specimen. For instance, the controller may automatically superimpose an "A" above the specimen to connote that such portion of the specimen faces the anterior portion of the patient, an "L" to the right of the specimen to connote that such portion of the specimen faces the lateral portion of the patient, and so on. Other examples include the use of different background colors in the image to connote various portions of the specimen, an avatar whose body position/orientation changes depending upon the particular orientation of the specimen in the image, and/or the like.

In addition to two-dimensional images, the system may be configured to obtain a series of images of the specimen as the controller is rotating the platform (and specimen) and then reconstruct the images into a three-dimensional dataset from which one or more three-dimensional image(s) may be obtained and manipulated by the operator on a display screen in any appropriate manner. Again, the controller may automatically impart one or more sets of graphical orientation indications into the generated three dimensional images (e.g., by way of letters, numbers, avatars, etc.) based on a particular rotational position of the platform about the rotation axis. In one arrangement, the controller may implement any appropriate inking protocol to automatically add color to different portions of the specimen depending on the particular portion of the specimen (e.g., red for posterior, green for inferior, etc.).

In one aspect disclosed herein, a system for use in obtaining images of a specimen includes a housing having an interior chamber; an imaging detector positioned relative to the housing; a source of electromagnetic radiation positioned relative to the housing; a specimen receiving platform disposed within the interior chamber, wherein the platform includes an orientation marker relative to which a particular portion of a specimen is positionable; and a controller that is configured to: trigger the source of electromagnetic radiation to generate a beam of electromagnetic radiation and send the beam through the specimen for receipt at the imaging detector; generate at least one image of the specimen based on the beam received at the imaging detector; generate a graphical indication on the at least one generated image of one or more orientations of corresponding portions of the specimen relative to one or more corresponding orientations of a patient's body, based on the positioning of the particular portion of the specimen related to the orientation marker; and present, on a display, the generated image along with a graphical indication of the one or more orientations.

In another aspect disclosed herein, an apparatus for use in imaging an object includes an upper portion that includes a receiving surface for receiving an object to be imaged; and a lower portion non-movably attached to the upper portion. The lower portion includes an indicator on an outer periphery thereof that is configured to convey to an operator a particular manner in which to position the object over the receiving surface of the upper portion; and a first rotation prevention device that is configured to engage with a corresponding second rotation prevention device of a rotatable platform (e.g., stage) of an imaging system to prevent relative rotation between the apparatus and the rotatable platform about a rotation axis.

In one embodiment, an imaging system disclosed herein may include a housing comprising an interior chamber; an imaging detector positioned relative to the housing; a source of electromagnetic radiation positioned relative to the housing; a rotatable platform disposed within the interior chamber and rotatable about a rotation axis, wherein the rotatable platform includes a second rotation prevention device; and the apparatus disposed over the rotatable platform such that the first and second rotation prevention devices engage to prevent relative rotation between the apparatus and the rotatable platform about the rotation axis.

In a further aspect disclosed herein, a method of generating images of a tissue specimen includes triggering a source of electromagnetic radiation to emit a beam of electromagnetic radiation along an axis through a tissue specimen and towards an imaging detector; generating at least one image with the received beam at the imaging detector; and superimposing, into or adjacent the at least one image by a system controller, a set of graphical indications that convey portions of a patient's body from which respective portions of the specimen were assumed to have been excised.

Various refinements may exist of the features noted in relation to the various aspects. Further features may also be incorporated in the various aspects. These refinements and additional features may exist individually or in any combination, and various features of the aspects may be combined. In addition to the exemplary aspects and embodiments described above, further aspects and embodiments will become apparent by reference to the drawings and by study of the following descriptions.

BRIEF DESCRIPTION OF THE DRAWINGS

For a more complete understanding of the present invention and further advantages thereof, reference is now made to the following Detailed Description, taken in conjunction with the drawings, in which.

DETAILED DESCRIPTION

Figure 1:
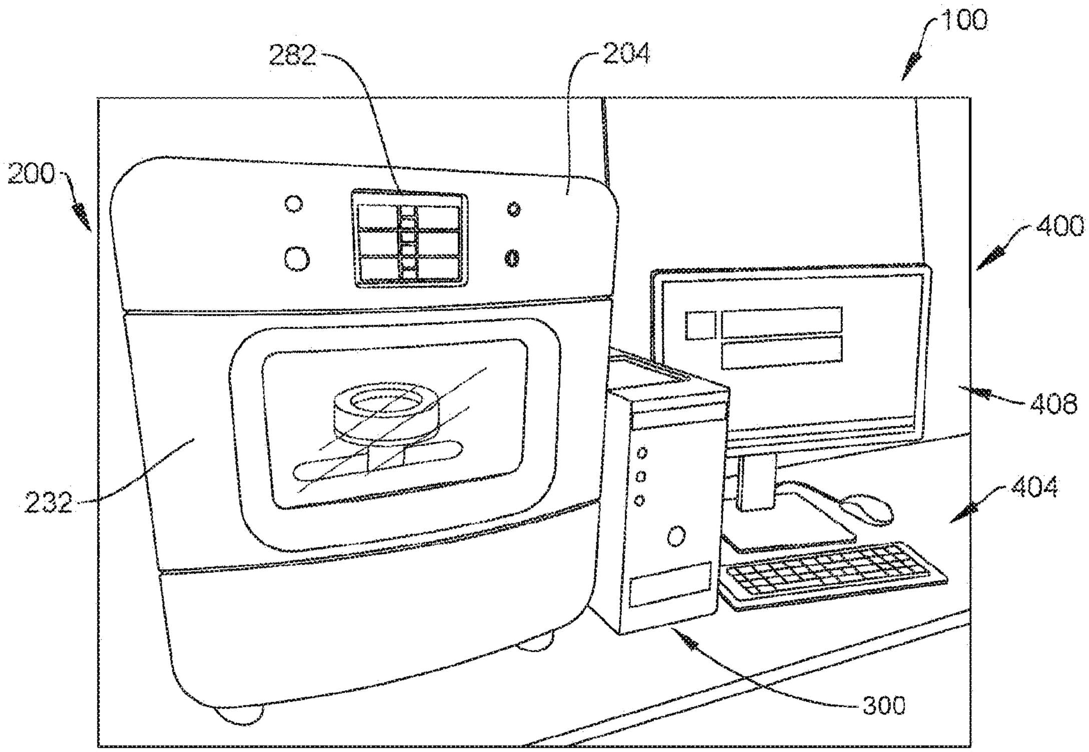
FIG. 1 is a perspective view of an imaging system that is configured to automatically obtain and provide two and three-dimensional digital images of objects such as tissue specimens, according to one embodiment.

Reference will now be made to the accompanying drawings, which assist in illustrating the various pertinent features of the various novel aspects of the present disclosure. In this regard, the following description is presented for purposes of illustration and description. Furthermore, the description is not intended to limit the inventive aspects to the forms disclosed herein. Consequently, variations and modifications commensurate with the following teachings, and skill and knowledge of the relevant art, are within the scope of the present inventive aspects.

Disclosed herein are apparatuses, systems, and methods ("utilities") for use in automatically graphically presenting, in or adjacent resulting images of an object such as a specimen, one or more orientation indications of the specimen relative to a patient's body for use by surgeons, radiologists, pathologists, and the like. Broadly, the disclosed utilities are configured to instruct a medical professional to position and orient a specimen in a particular manner in preparation for imaging such that the graphical orientation indications imparted into the resulting images automatically align with the respective corresponding portions of the specimen in the images. For instance, the various orientation indications may indicate a different respective portion or location of a patient's body from which the specimen was extracted. In one arrangement, the particular portion of the specimen may be oriented in a receiving surface of a platform relative to a particular fixed portion of the system (e.g., x-ray source) in preparation for imaging and then a computing system or controller (e.g., logic) of the system may be configured to impart relative orientation indications into resulting images.

With initial respect to FIGS. 1-4, an imaging system 100 is disclosed in which the specimen orientation utilities disclosed herein may be implemented. The system 100 is broadly configured to automatically obtain and provide two dimensional (e.g., orthogonal) digital images and three-dimensional (e.g., reconstructed) digital images of various types of objects such as tissue specimens. The obtained images allow for tissue margin verification to be obtained in the surgery room, thus enabling cases to be completed faster, limiting the time patients need to be under examination, and limiting patient recalls. Many aspects of the system 100 are disclosed in International App. No. PCT/US2018/050490, entitled "IMAGING SYSTEM WITH ADAPTIVE OBJECT MAGNIFICATION," filed on Sep. 11, 2018, and assigned to the assignee of the present application, the entirety of which is incorporated herein by reference.

The system 100 generally includes a shielded imaging cabinet 200, a computing system 300 (e.g., service, desktop computer, etc., including processor(s), memory, etc.), and one or more peripherals 400 electrically interconnected to the computing system 300 such as input devices 404 (e.g., keyboard, mouse), output devices 408 (e.g., monitor or display), and the like. The computing system 300 may generally be configured to receive input from a technician, physician, or the like regarding an object to be imaged (e.g., patient information, object information, etc.) and store the same, initiate an imaging procedure based at least in part on the received input (e.g., trigger source 220 or electromagnetic radiation (e.g., x-rays) to emit beams 222 through the object for receipt at a detector 224), move an object imaging platform on which the object is disposed into one or more various positions within the cabinet 200 as discussed more fully below), receive and process signals from the x-ray detector, and generate various 2D and 3D images of the object for presentation to the physician or the like (e.g., on output device/monitor 408) for use in tissue margin verification. The computing system 300 may allow the physician or the like to view the 2D and 3D images on a screen and slice through the 3D image at almost any position to see internal details of the same.

While the computing system 300 is illustrated as being separate from the cabinet 200, the computing system 300 may in other arrangements be appropriately combined with the cabinet 200 into a single unit. In other arrangements, the computing system 300 may be disposed remote from the cabinet 200 such as in a separate room or even geographically remote and in communication therewith by one or more networks (e.g., LAN, WAN, Internet) or may be distributed among a plurality of computing systems (e.g., servers, networks, etc.). In any case, all references to "computing system" or similar (e.g., controller) herein are intended to encompass one or processors or processor cores that are configured to execute one or more sets of computer-readable instruction sets to carry out the various determinations and functionalities disclosed herein (e.g., determining a position of an object within the interior chamber 208 of the cabinet 200, triggering motion control apparatus 500 to move the object within the cabinet based on the determined position, triggering electromagnetic radiation source 220 to emit one or more electromagnetic radiation beams 222 through object, generating image data sets based on electromagnetic radiation beams received at detector 224, and the like).

Broadly, the cabinet 200 includes a housing 204 that generally defines an interior chamber 208 for receiving an object (e.g., tissue specimen) on an object receiving surface 216 of an object holder or platform 212 that is movable within the interior chamber 208 relative to the source 220 of electromagnetic radiation (e.g., beam 222) and the imaging detector 224. The imaging detector 224 is configured to receive electromagnetic radiation emitted from the source 220 after passing through an object (not shown) received on the object receiving surface 216. The platform 212 may be at least partially constructed from any appropriate radiolucent or low radio-density material (e.g., as one example, polymeric foam) to substantially eliminate or at least reduce attenuation of a beam of electromagnetic radiation passing through the platform 212; this arrangement thus substantially eliminates or at least reduces the likelihood of the platform 212 appearing in an image of the object and correspondingly increases the quality (e.g., contrast, resolution, etc.) of the image (e.g., for use in verifying tissue margins, identifying suspicious locations or areas in the excised tissue specimen to be subsequently analyzed by a pathologist, and/or the like). Further details regarding how the platform 212 and system controller (e.g., computing system 300) facilitate the presentation of graphical indications of specimen orientations in resulting images will be discussed in more detail below.

Figures 2A, 2B:
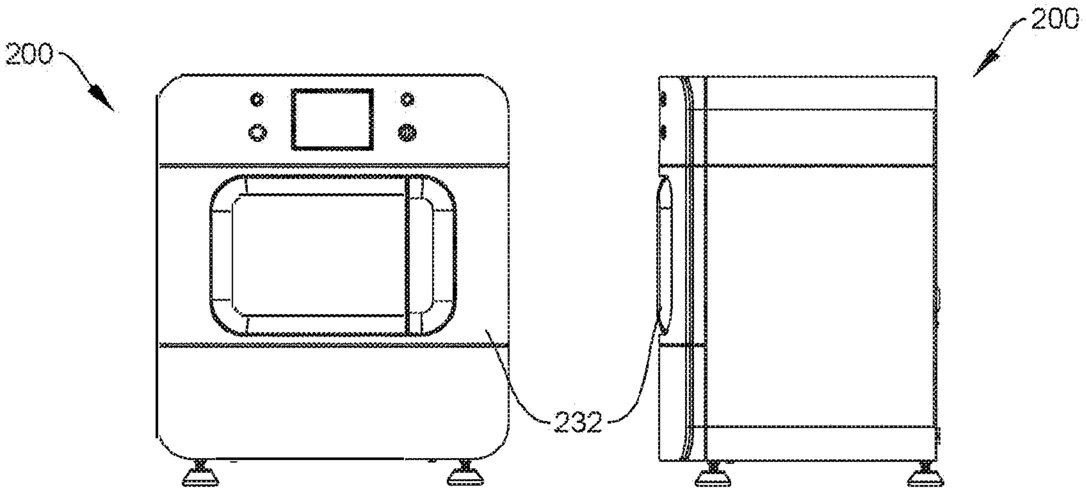
FIGS. 2*a*-2*b* are front and side views of an imaging cabinet of the system of FIG. 1.

The housing 204 may generally include any appropriate arrangement of walls 228, electromagnetic shielding (e.g., lead sheets, etc.), brackets, and other componentry (not all shown or labeled in the interest of clarity) to define the interior chamber 208, limit electromagnetic radiation from escaping or leaking from the housing 204, and non-movably secure the source 220 and detector 224 relative to the housing 204 (i.e., the source 220 and detector 224 are non-movable relative to the walls 228, brackets, etc. of the housing 204 during imaging procedures). Furthermore, the housing 204 includes a shielded access member 232 (e.g., door) that is movable between an open position (as shown in FIG. 3) and a closed position (as shown in FIGS. 1 and 2*a*) to provide access to the interior chamber 208 so as to place objects therein and remove objects therefrom.

Figure 3:
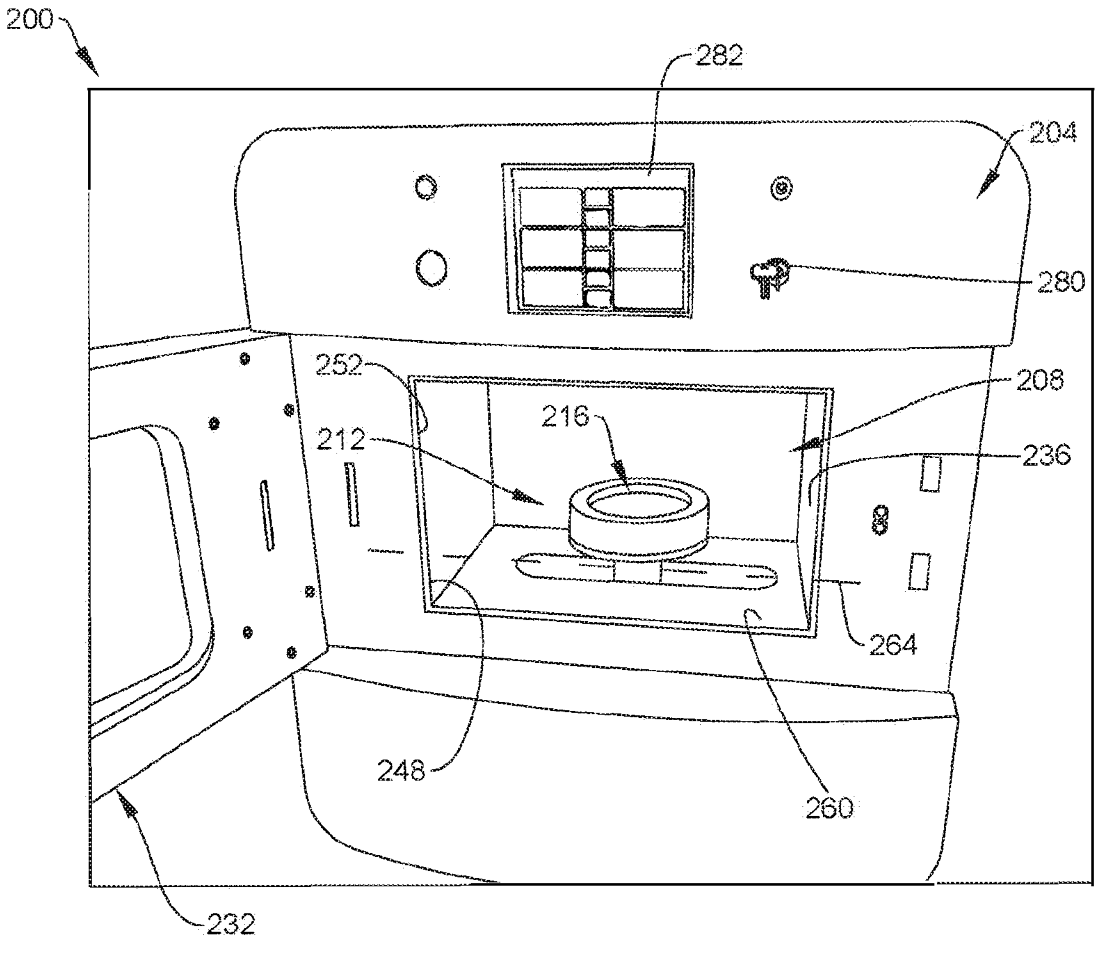
FIG. 3 is a perspective view of the imaging cabinet of FIGS. 2*a*-2*b* with a door of the cabinet in an open position and exposing an interior chamber of the cabinet.
Figure 4:
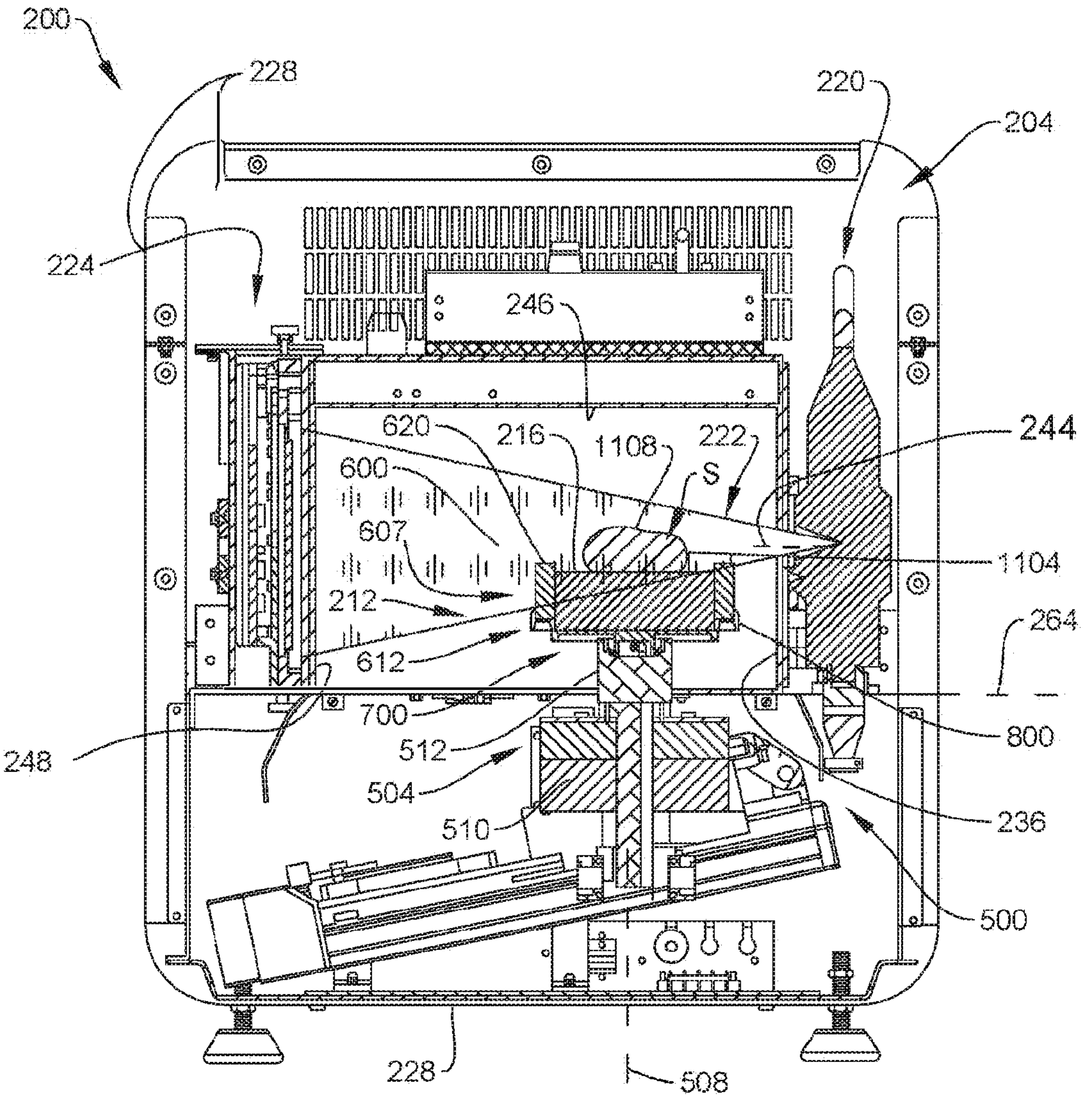
FIG. 4 is a sectional view through the imaging cabinet of FIGS. 2*a*-2*b*.

With reference now to FIGS. 3-4, the source 220 may be rigidly fixed relative to a first sidewall or portion 236 of the housing 204 in any appropriate manner such that electromagnetic radiation beams 222 (e.g., x-ray cone beam) emitted from the source 220 may pass through an opening or aperture (not labeled) in the first side portion 236 along an axis 244 (e.g., a central axis) towards the detector 224. The detector 224 may be rigidly fixed relative to an opposite second sidewall or portion 248 of the housing 204 in any appropriate manner such that the electromagnetic radiation beams 222 emitted along the axis 244 may be received through an opening or aperture (not labeled) in the second side portion 248 at the detector 224. Each of the source 220 and the detector 224 may be appropriately electrically interconnected to the computing system 300 so as to be appropriately controlled by one or more controllers or processors (e.g., executing any appropriate computer-readable instructions or logic as stored on any appropriate memory structure) during any appropriate imaging procedures.

The cabinet 200 may also include a motion control mechanism or apparatus 500 to facilitate obtaining two- and three-dimensional images of a specimen. The motion control mechanism or apparatus 500 may broadly be configured to move an object received or placed on the object receiving surface 216 relative to the source 220, the detector 224, and the axis 244 along which the beams 222 are emitted from the source 220 to the detector 224. In one embodiment, the motion control mechanism 500 may include a rotary drive 504 that is configured to rotate the platform 212 (and thus the object receiving surface 216 and an object received thereon) about a rotational axis 508 that is substantially perpendicular to the axis 244 along which the beams 222 travel.

For instance, the rotary drive 504 may include a motor 510 that is configured to rotate a shaft assembly 512 in first and/or second directions about the rotational axis 508 under control of the computing system 300. The shaft assembly 512 may be rigidly or non-movably attached to the platform 212 in any appropriate manner such that rotation of the shaft assembly 512 induces simultaneous corresponding rotation of the platform 212 (and thus the object receiving surface 216 and the object placed thereon) about the rotational axis 508.

In operation, and after an object (e.g., specimen) has been placed on the object receiving surface 216 of the platform 212, the computing system 300 (e.g., controller) may trigger the source 220 to emit a beam 222 of electromagnetic radiation along the axis 244 through the object for receipt at the detector 224, whereupon the received electromagnetic radiation signals may be appropriately processed by the computing system 300 or the like for generation of a first two-dimensional image of the object with the object in a first rotational position. In one arrangement, the first rotational position of the object and platform 212 may be considered a "home" position (e.g., as in FIG. 5*a*).

As discussed above, orthogonal and/or three-dimensional imaging of the object may be used to verify tissue margins in the case of tissue specimens, detect defects in the case of electrical devices, and the like. In this regard, the computing system 300 may trigger the motion control apparatus 500 to rotate the platform 212 and object by 90° about the rotational axis 508 from the home or first rotational position to a second rotational position and then trigger the source 220 to emit a beam 222 of electromagnetic radiation along the axis 244 through the object for receipt at the detector 224 for generation of another (orthogonal) two-dimensional image of the object with the object and platform 212 in the second rotational position.

Additionally or alternatively, the computing system 300 may trigger the motion control apparatus 500 to rotate the platform 212 and object and simultaneously trigger the source 220 to emit a beam 222 of electromagnetic radiation along the axis 244 through the object as it is rotating about the rotational axis 508. The computing system 300 may be configured to receive and process detected electromagnetic radiation signals from the detector 224 as the object is rotating about the rotational axis 508 to generate a plurality of two dimensional images (e.g., several times per second or more) which may then be reconstructed by the computer device 300 or the like into a three-dimensional data set and a corresponding three-dimensional image of the object. The three-dimensional images can be used in combination with or separate from the two-dimensional images as part of tissue margin verification, defect detection, and the like.

In some situations, a maximum outline of the object may not substantially fill the area of the beam (e.g., where the area of the beam extends within a reference plane that is substantially parallel to the first and second side walls 236, 248 of the housing 204 and perpendicular to the beam axis 244) due to the size or dimensions of the object, due to the positioning of the object receiving surface 216 relative to the beam axis 244, and/or the like which may otherwise result in inaccurate or distorted images of the object. In another characterization, a centroid of the object may not substantially intersect the beam axis 244 or the centroid may substantially intersect the beam axis 244 but the object may be positioned too far away from the source 220 to obtain images of an appropriate magnification. In this regard, the motion control apparatus 500 (under control of the computing system 300) may be configured to linearly move the object receiving surface 212 and object thereon along an axis 264 relative to the source 220, the detector 224, and the beam axis 244 so as to move the centroid of the object into substantial intersection with the beam axis 244 and/or to move the object closer to the source 220 for use in obtaining higher quality images of the object. Further details regarding the ability of the motion control apparatus 500 to move the object receiving surface or platform 212 in this manner may be found in International App. No. PCT/US2018/050490, the entirety of which is incorporated herein by reference.

As discussed herein, the present disclosure includes various specimen orientation utilities that are configured to automatically graphically present, into or alongside resulting images of the specimen, one or more orientation indications of an object (such as a tissue specimen) relative to a patient's body for use by surgeons, radiologists, pathologists, and the like. With reference now to FIGS. 4 and 5*a*-5*c*, the system 100 may include at least one indicator 800 (e.g., tab, projection, print, marker, wording, radiopaque ink, LED) to aid an operator (e.g., surgeon) in positioning a specimen S such that a first particular portion of the specimen (e.g., portion facing the "caudal" direction of the patient before excision) faces towards a first particular fixed portion of the system (e.g., source 220). For instance, the indicator 800 may be physically disposed on a portion of the platform 212 (e.g., such as on an outer periphery 214) such that, when the operator positions the specimen S over the receiving surface 216 of the platform 212 with the first particular portion facing, near, and/or adjacent the indicator 800, the first particular portion of the specimen may thus also face the first particular fixed portion of the system 100 with the platform 212 in its home position (as in FIG. 5*a*).

Stated differently, the indicator 800 may be aligned with or face towards the first particular fixed portion of the system 100 (e.g., along or parallel axis 244) in the home rotational position of the platform 212 about the rotational axis 508. While the indicator 800 is illustrated as being physically disposed on the platform 212, the indicator may in another embodiment be digitally projected onto the platform 212 to be aligned with or face towards the first particular fixed portion of the system 100 in the home position of the platform 212. In a further embodiment, the indicator 800 may be disposed (e.g., physically or digitally) remote from the platform 212 such as on any appropriate portion of the housing walls. While not shown, one or more additional indicators 800 may be included on or over the platform 212 or other portions of the cabinet 200 towards which the operator is intended to direct additional portions of the specimen S to facilitate presentation of orientation indications in resulting images by the system controller.

With additional reference now to FIGS. 6*a*-6*c* and 7*a*-7*b*, the platform 212 may in one arrangement include separate upper and lower portions 600, 700 that are configured to rotate as a single unit about the rotation axis 508. For instance, the lower portion 700 may be in the form of a stage or table that is rigidly attachable to the shaft assembly 512 in any appropriate manner while the upper portion 600 may be in the form of a disposable tray or the like that includes the receiving surface 216 on a top portion 607 thereof and that is configured to be supported by the lower portion 700. The platform 212 may also include a rotation prevention mechanism that is configured to inhibit relative rotation between the upper and lower portions 600, 700 so that they can rotate as a single unit about the rotation axis 508 (e.g., so that a torque applied by the rotary drive 504 to the lower portion 700 about rotational axis 508 is automatically applied to the upper portion 600).

In one arrangement, the rotation prevention mechanism may be in the form of a first rotation prevention device 604 on a bottom portion 608 of the upper portion 600 and a corresponding second rotation prevention device 704 of the lower portion 700. For instance, the first rotation prevention device 604 may be in the form an opening having a non-circular outer periphery as defined by walls 616 projecting from the bottom portion 608 of the upper portion 600. The second rotation prevention device 704 may be in the form of a member or key having a corresponding non-circular outer periphery 708 that is configured to be received in the opening (e.g., see FIG. 4). In one arrangement, the at least one indicator 800 may be disposed on the upper portion 600 and the first and second rotation prevention devices 604, 704 may be configured to engage (and thus prevent relative rotation between the upper and lower portions 600, 700) just as the at least one indicator 800 is directed and/or facing towards the first fixed portion of the system (e.g., towards the source 220). See FIG. 4.

While the first and second rotation prevention devices 604, 704 are illustrated as being a respective corresponding non-circular opening and key, the rotational prevention mechanism could also be arranged versa. Furthermore, the rotation prevention mechanism may take various other forms that allow for the selective prevention of relative rotation between the upper and lower portions 600, 700 (e.g., such as when the indicator 800 is directed or facing towards the first particular fixed portion of the system 100).

In one arrangement, one or more portions of the platform 212 (e.g., such as the top portion 607 of the upper portion 600) may be constructed of any appropriate radiolucent or low radio-density material (e.g., as one example, polymeric foam) to substantially eliminate or at least reduce attenuation of the beam 222 of electromagnetic radiation passing through the platform 212. For instance, see beam 222 passing through upper portion 600 of the platform 212 in FIG. 4. In one embodiment, the top portion 607 may include a circumferential lip or rim 620 (e.g., configured to surround the rotation axis 512 when the upper portion 600 is disposed over the lower portion 700) that is configured to contain a specimen S received on the receiving surface 216. The rim 620 can also serve as a visual indicator to an operator as to where to position the specimen S such that the specimen S remains in the field of view of the beam 222 during imaging procedures. In one arrangement, the indicator 800 may be disposed on the bottom portion 608 of the upper portion 600 to be outside of the field of view of beam 222 during imaging procedures. See FIG. 4. In one embodiment, the bottom portion 608 of the upper portion 600 may be constructed of one or more materials that at least partially attenuate imaging signals (e.g., such as in the case where imaging beams 222 are configured to not pass through the bottom portion 608, see FIGS. 4, 5*a*, 5*b*). Furthermore, the top and bottom portions 607, 608 of the upper portion 600 may be attached in any appropriate manner so as to be generally non-movable relative to each other and thus function as a single unit (e.g., when the system 100 triggers the rotary drive 504 to rotate the lower portion 700, such torque is automatically transferred to the top portion 607 via the bottom portion 608 of the upper unit 600).

To more fully understand the various functionalities of the disclosed system, additional reference will now be made to FIG. 10 which presents a flow diagram of a method 1000 of positioning a specimen onto a receiving surface of an imaging system and operating the system to obtain images of the specimen with orientation indictors in or with the images. While certain steps are shown in a particular order in FIG. 10, it is to be understood that more or fewer steps may be included in the same or different order than shown in FIG. 10.

Figure 5A:
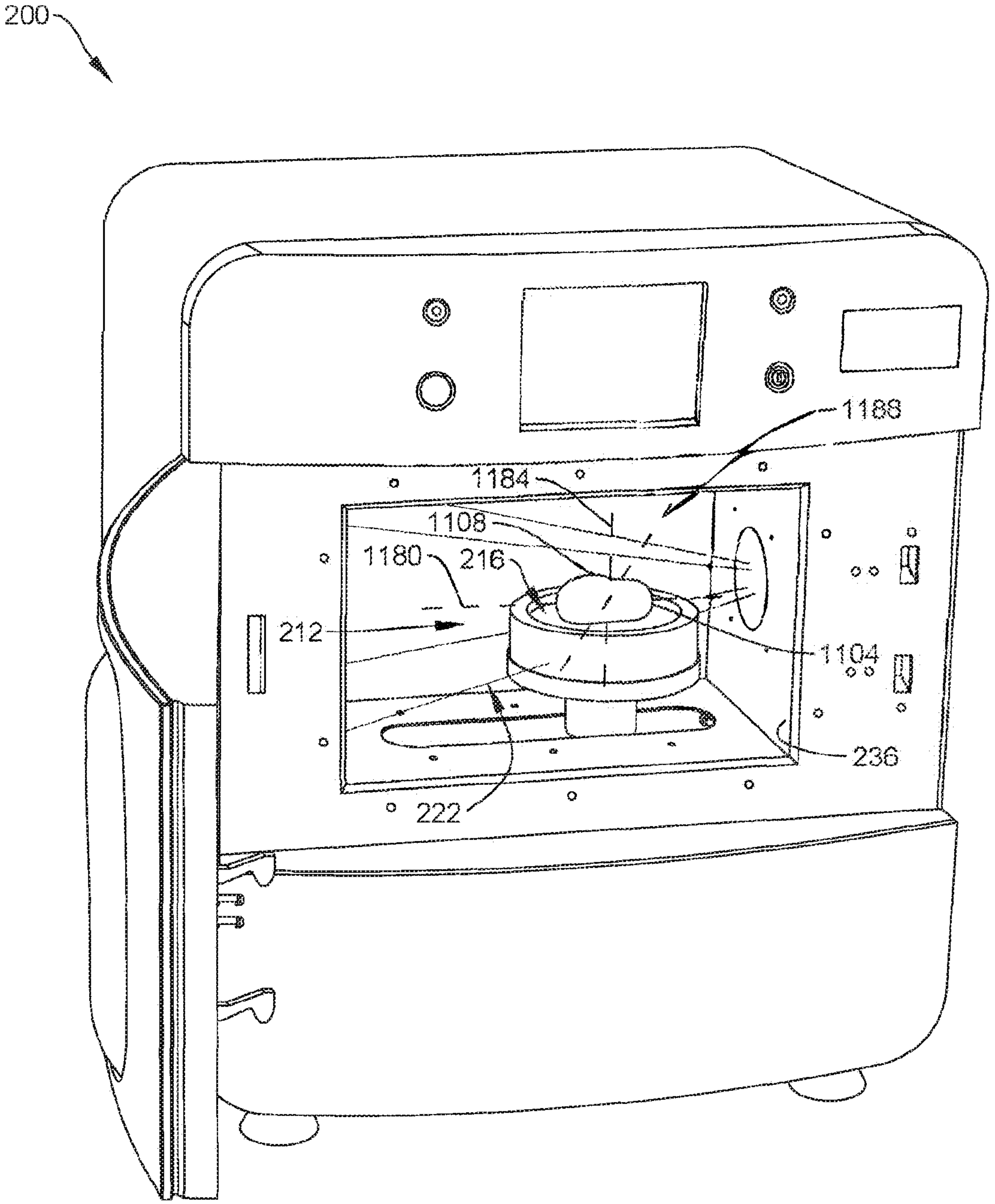
FIG. 5*a* is a perspective view of the cabinet of FIG. 1 with the door removed for clarity and illustrating a specimen receiving platform in a home position.
Figure 5B:
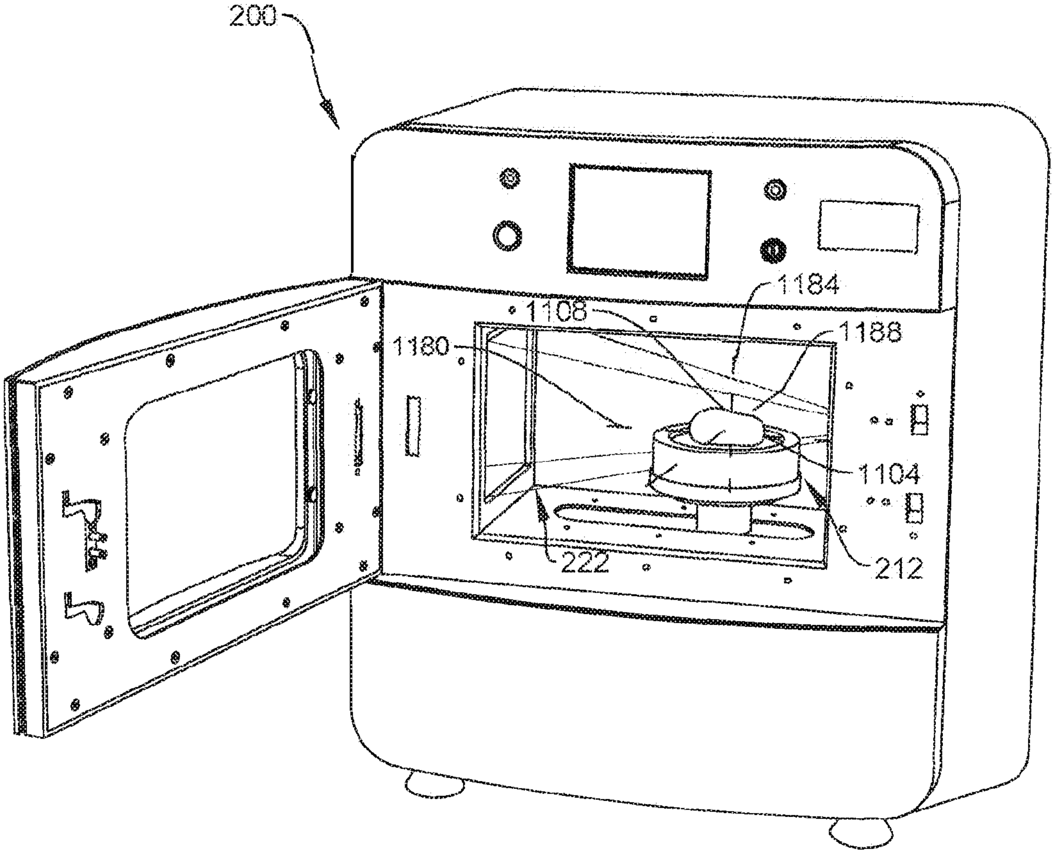
FIG. 5*b* is similar to FIG. 5*a* but from a different perspective.
Figure 5C:
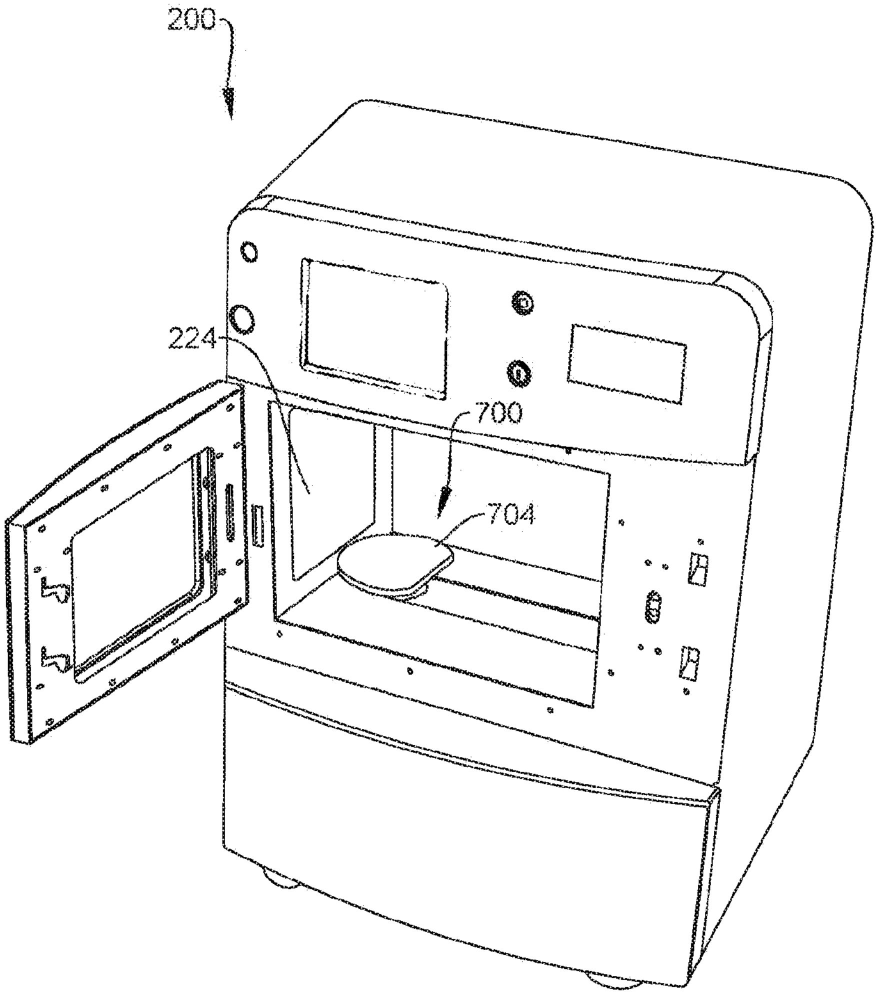
FIG. 5*c* is a perspective view similar to FIG. 5*b* but with a receiving tray removed from a receiving stage of the platform.
Figures 6A, 6B, 6C, 7A, 7B:
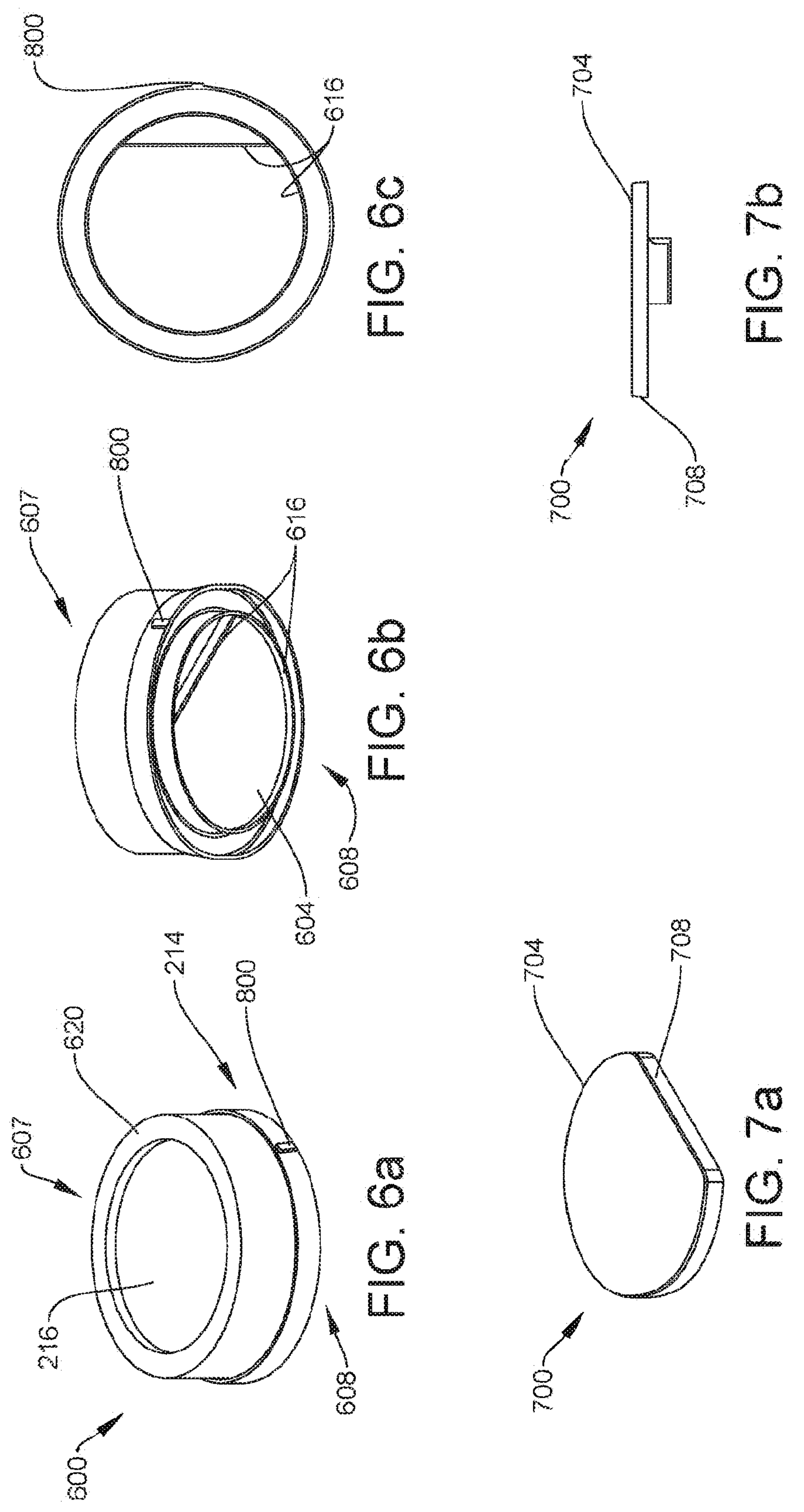
FIGS. 6*a*-6*c* present various views of the receiving tray of the platform.
FIGS. 7*a*-7*b* present various views of a receiving stage of the platform.

At step 1004, the method 100 may include positioning a specimen S onto a receiving surface (e.g., receiving surface 216) of an imaging system platform (e.g., platform 212) in its "home" position such that a first particular portion of the specimen (e.g., the portion of the specimen facing the caudal portion of the patient before excision) faces a first particular fixed portion of the imaging system and such that a second particular portion (e.g., the portion of the specimen facing the anterior portion of the patient before excision) faces a second particular fixed portion of the imaging system. With reference to FIGS. 4, 5*a*, and 5*b*, for instance, the specimen S may be placed on the receiving surface 216 so that a first particular portion 1104 (e.g., caudal) of the specimen S generally faces the source 220 (or first sidewall 216 of housing 204) and so a second particular portion 1108 (e.g., anterior) of the specimen S generally faces upwardly towards an upper wall 246 of housing 204 that generally interconnects the first and second sidewalls 236, 248.

To aid the operator in positioning the specimen S in this manner, the operator may position the first particular portion 1104 generally towards or in alignment with at least one indicator such as indicator 800 and/or with any other appropriate indicator that facilitates facing the first particular portion 1104 towards the first particular fixed portion of the imaging system with the platform 212 in its home position. In the event that the platform 212 includes the upper and lower portions 600, 700 disclosed herein and the upper portion 600 is separated from the lower portion 700, the operator may position the specimen S over the receiving surface 216 of the upper portion 700 taking care to position the first particular portion 1104 towards or adjacent the indicator 800 and the second particular portion 1108 upwardly or in other words opposite the receiving surface 216. The operator may thereafter position the bottom portion 608 of the upper portion 600 over the lower portion 700 so that the first and second rotation prevention devices 604, 708 engage to inhibit relative rotation between the upper and lower portions 600, 700 (which may require an initial rotation of the upper portion 600 relative to the lower portion 700 until the first and second rotation prevention devices 604, 708 engage). As discussed herein, the first and second rotation prevention devices 604, 708 may be configured to engage to prevent relative rotation there between with the indicator 800 and thus first particular portion 1104 of the specimen S being directed towards the first particular fixed portion of the system 100 and the second particular portion 1108 of the specimen S being directed towards the second particular fixed portion of the system 100. In this regard, the indicator 800 may serve as a proxy for the first particular fixed portion of the system in the home position of the platform 212 when the upper and lower portions 600, 700 of the platform 212 are separated. Furthermore, in the case where the platform 212 includes a rim 620, the operator may also ensure that the specimen Sis fully contained within the rim 620.

With reference again to FIG. 10, the method 1000 may then generally include operating 1008 the imaging system (e.g., imaging system 100 or 200) to perform imaging of the specimen and then receiving 1060, on a display screen, images of the specimen that include one or more orientation indicators superimposed onto or alongside the images to convey to the operator how various portions of the specimen in the images relate to the patient's body from which the specimen was excised. In the case of two-dimensional imaging 1012, the method 1000 may generally include operating 1016 the source 220 to direct a beam 222 through the specimen S for receipt at the detector 224 and generating a first image. The operating step 1016 may occur with the specimen S positioned as in step 1004 and the platform 212 being in its home position about the rotation axis 508. For instance, see left image in FIG. 8.

The method 1000 may then include rotating 1020 the platform 212 (and thus specimen S) from the home position to a second rotational position about the rotation axis 508 such that another particular portion of the specimen S faces the first particular fixed portion of the system 100. For instance, in the case where the platform 212 is rotated 1020 by 90 degrees, the another particular portion of the specimen S may be a medial or lateral portion of the specimen S (e.g., the portion of the specimen S that faces the medial or lateral portion of the patient before excision, assuming that the surgeon or radiologist had placed the caudal portion of the specimen S towards the first particular fixed portion of the system 100 in the home or first rotational position of the platform 212). The method 1000 may then include operating 1024 the source 220 to direct a beam 222 through the specimen S (in its second position) for receipt at the detector 224 and generating a second image. For instance, see right image in FIG. 8. While FIGS. 4, 5*a*, and 5*b* illustrate the platform 212 and specimen S being positioned along axis 264 proximate source 220, two dimensional images may be taken with the platform 212 and specimen S being positioned along axis 264 proximate detector 224 (e.g., in the position shown in FIG. 5*c*).

The method 1000 may then include superimposing 1028, into or alongside the first and second images, respective first and second sets of graphical orientation indications based on the respective rotational position of the platform 212 for receipt 1060 by the operator, doctors, and/or other personnel and use thereof for various analytical purposes (e.g., margin verification, etc.). In the first image which was obtained with the platform 212 in its first or home rotational position, the system controller may be configured to automatically impart into or alongside the first image a first set of graphical anatomical indications 1200 (e.g., anterior portion at top of image, lateral on side of image, etc.) that are configured to convey the assumed position of various portions of the specimen Sin the first image. In the second image which was obtained with the platform 212 in a second rotational position that is perpendicular to the home position, the system controller may be configured to automatically impart into or alongside the second image a second set of graphical anatomical indications 1200 that are at least partially different than the first set of graphical anatomical indications 1200.

As discussed previously, the various anatomical axes are perpendicular to each other. Accordingly, assuming that the platform 212 is rotated by 90 degrees between the first and second rotational positions, the second set of graphical orientation/anatomical indications imparted into or with the second image may be 90 degrees rotated relative to the first set of graphical orientation/anatomical indications. For instance, the anterior and posterior indications 1200 may still be positioned near the top and bottom of the second image as the rotation axis 508 about which the platform 212 was rotated is parallel to a reference axis 1184 interconnecting the anterior and posterior indications 1200 (see FIGS. 5*a*-5*b*). However, the cranial and caudal graphical indications 1200 (e.g., interconnected by a reference axis 1180) may now be positioned on the sides of the second image and medial and lateral graphical indications (e.g., interconnected by a reference axis 1188) may no longer be in the second image as these portions face towards the view and away from the viewer. In practice, the first, second, and third reference axes 1180, 1184, 1188 may not necessarily be visible in the images so as to not obscure the images as part of analysis of the images. While the superimposing 1028 is illustrated and discussed as occurring after both of the image generation steps, the superimposing 1028 could alternatively occur after the first image generation step for the first image and before the second image generation step, and then again after the second image generation step.

Figure 8:
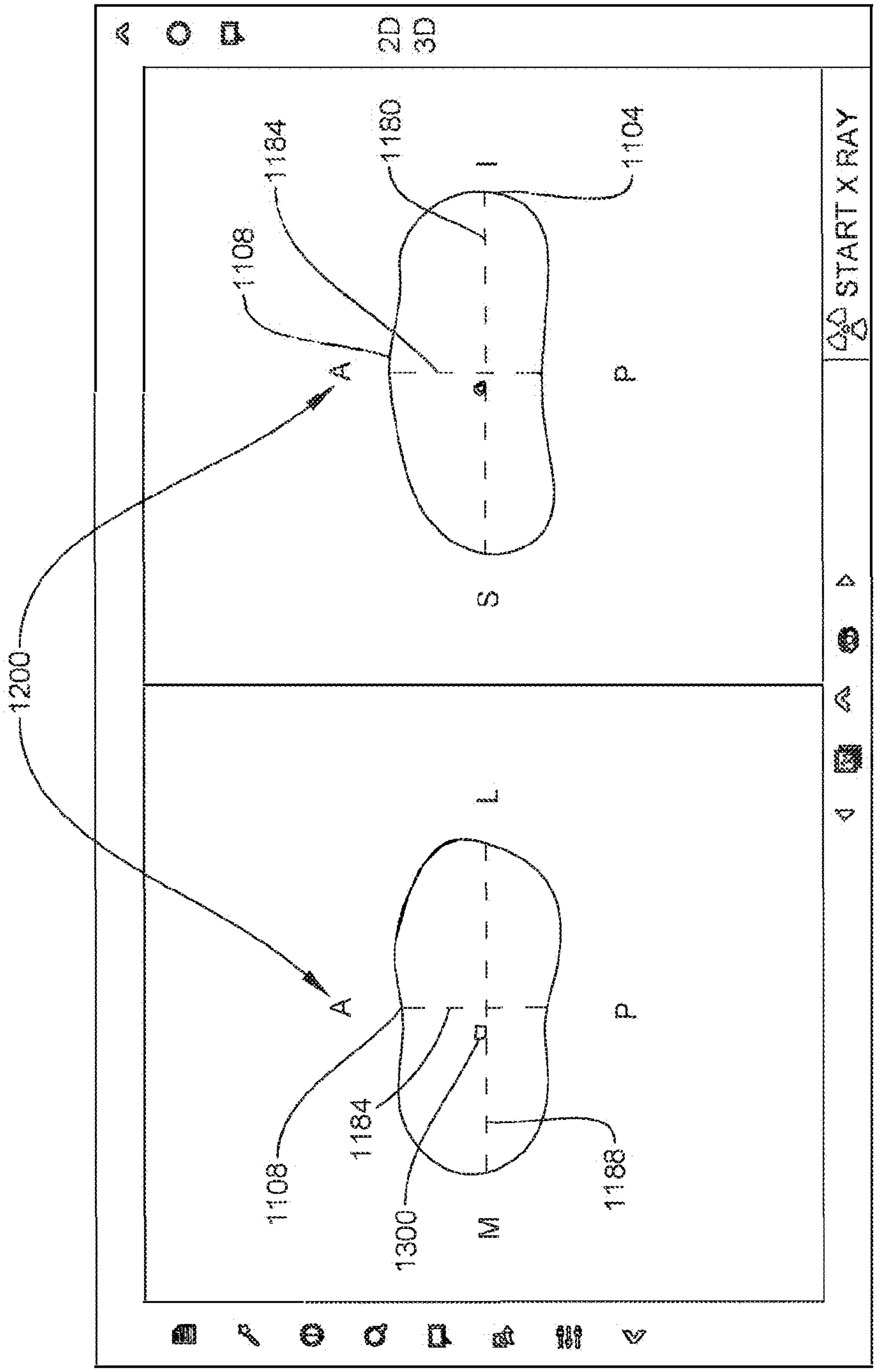
FIG. 8 presents two-dimensional images of a specimen that include specimen orientation markers generated by the present system.

As illustrated in FIG. 8, the various indications 1200 may be in the form of lettering or text adjacent the respective particular portions of the specimen S where, for instance, "A" stands for anterior, "P" stands for posterior, "M" stands for medial, "L" stands for lateral, "S" stands for superior, and "I" stands for inferior. In one arrangement, the indications 1200 may be presented on the display and generally adjacent but spaced from the actual images of the specimen S so as not to interfere with analysis of the images. Other examples of indications 1200 include the use of different background colors in the image to connote various portions of the specimen S, an avatar whose body position/orientation changes depending upon the particular orientation of the specimen in the image, and/or the like.

Figure 10:
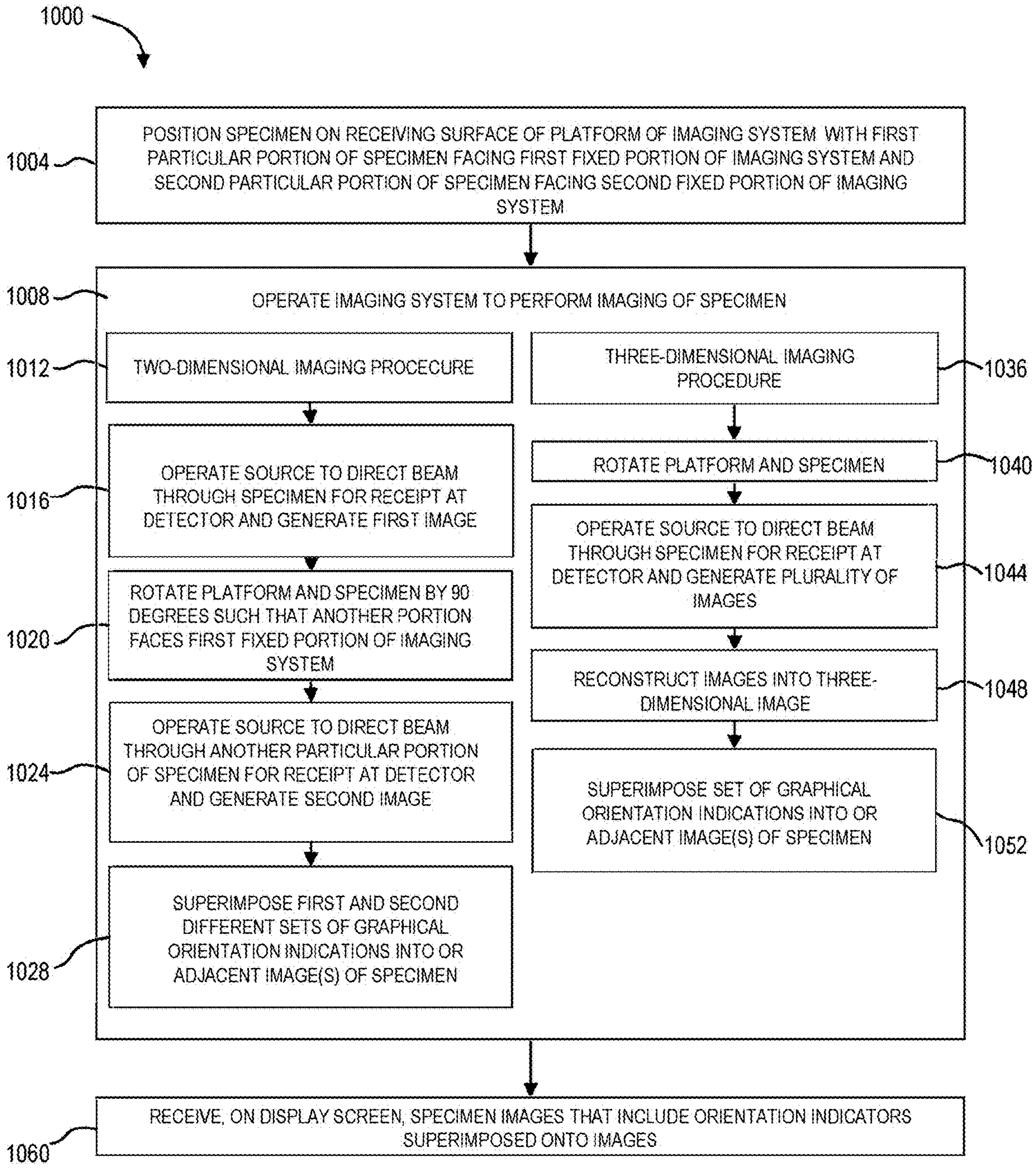
FIG. 10 is a flow diagram of a method of positioning a specimen onto a receiving surface of an imaging system and operating the system to obtain images of the specimen with orientation indictors in the images.

The operating step 1008 of FIG. 10 may alternatively or additionally include conducting 1036 a three-dimensional imaging procedure which generally includes rotating 1040 the platform 212 and specimen S; operating 1044 the source 220 to direct a beam 222 through the specimen S for receipt at the detector 224 and generating a plurality of images; reconstructing the images 1048 the images into a three-dimensional dataset to obtain a three-dimensional image; and superimposing 1048, into or alongside the three-dimensional image, one or more sets of graphical orientation indications based on the respective rotational position of the platform 212 for receipt 1060 by the operator, doctors, and/or other personnel and use thereof for various analytical purposes (e.g., margin verification, etc.).

Figure 9:
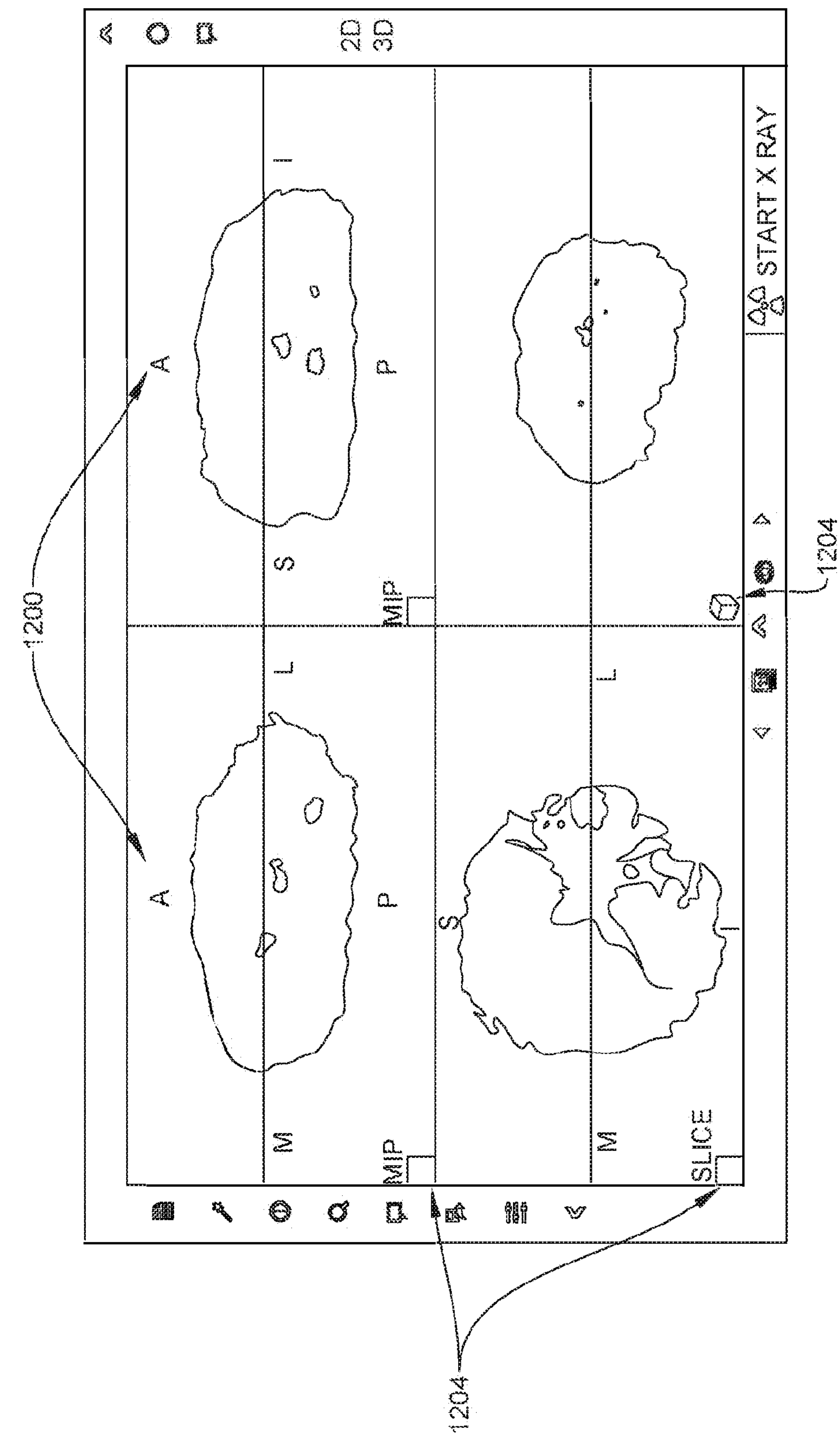
FIG. 9 presents two- and three-dimensional images of a specimen that include specimen orientation markers generated by the present system.

With reference to FIG. 9, the top two images present different maximum intensity projection (MIP) images from the generated three-dimensional dataset that include superimposed indications 1200 that convey the relative orientations of different portions of the specimen to the patient's body from which the specimen was excised. The bottom left image is a slice through the specimen S while the bottom right image is a three-dimensional image that is manipulatable by an operator (e.g., by clicking on the image and dragging). Again, one or more indications 1200 may be superimposed. In one arrangement, one or more second indications 1204 corresponding to any appropriate inking protocol may be superimposed into the images (e.g., where red corresponds to posterior, green corresponds to inferior, yellow corresponds to medial, etc.). For instance, the indication 1204 in the three-dimensional image (lower right image) may be a small cube color coded to the particular inking protocol that automatically rotates in conjunction with an operator manipulating the image to convey the particular portion of the image being viewed.

The various two- and three-dimensional images obtained herein (e.g., those in FIGS. 8 and 9) may be stored in any appropriate Digital Imaging and Communications in Medicine (DICOM) format and sent to radiology, pathology, and/or the like in any appropriate manner.

Figure 11:
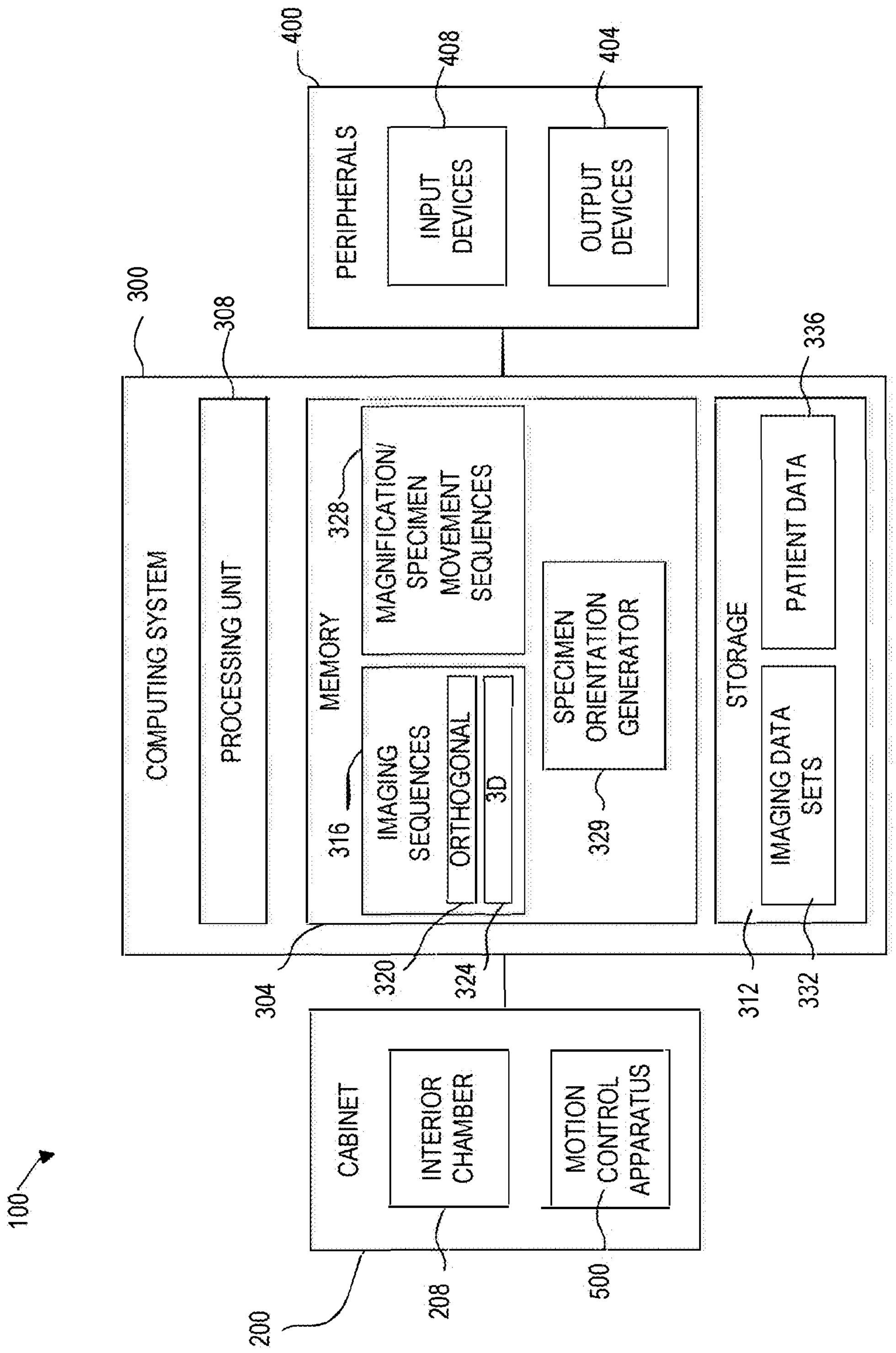
FIG. 11 is a schematic block diagram of the system of FIG. 1.

FIG. 11 presents a simplified schematic block diagram of the system 100 and illustrating some details of the computing system 300 to implement some of the functionalities disclosed herein. It is noted that not all components of the system 100 are illustrated in FIG. 11 in the interest of clarity. As shown, the computing system 300 may include at least one memory device 304 (e.g., RAM or other volatile memory), at least one processing unit 308 (e.g., processor(s), processing device(s), processor core(s), multiprocessor(s), etc.) that executes computer-readable instructions (e.g., logic, sequences, etc.) from the memory device 304, and at least one storage device 312 (e.g., hard disk, flash memory, or other non-volatile memory).

For instance, the memory device 308 may include one or more imaging sequences 316 such as orthogonal imaging sequences 320 and 3D imaging sequences 324 that are configured to be executed by the processing unit 308 to trigger the electromagnetic source 220 to emit beams of electromagnetic radiation and to collect signals from the detector 224 for use in generating and storing corresponding imaging data sets 332 in storage 312 and displaying the same on an output device 404 (e.g., monitor). The memory device 308 may also include one or more magnification/object movement sequences 328 that are configured to be executed by the processing unit 308 to trigger the motion control apparatus 500 to rotate the object receiving surface 212 and object O (e.g., specimen S) about rotation axis 508 and/or move object receiving surface 212 and object O along one or more of the above-discussed axes as part of imaging of the object O. Furthermore, the memory device 308 may include a specimen orientation generator 329 (e.g., logic, instructions) that is broadly configured to superimpose one or more indications of specimen orientations into resulting images as discussed herein. Any appropriate patient data 336 (e.g., name, ID, object location, etc.) may also be stored in any appropriate format or structure.

The processing unit 308 may execute the various sequences 316, 328, generator 329, etc. independently or concurrently as appropriate, consistent with the teachings presented herein. It is to be understood that the various sequences 316,328, generator 329, etc. (logic, computer-readable instructions) may be loaded from any appropriate non-volatile storage (e.g., storage 312 or elsewhere) before being appropriately loaded into memory 304 for execution by processing unit 308. In one arrangement, the memory device 304 and processing unit 308 may function as a controller that is configured to trigger one or more components of the system 100 (e.g., motion control apparatus 500, source 220, etc.) based on inputs from a user (e.g., to initiate an imaging sequence), based on measurements or readings obtained by the computing system 300, etc.

The description herein has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. In one arrangement, an artificial "false floor" may be superimposed into two-dimensional images (e.g., by computing system/controller 300) to simulate the interface between the specimen and the receiving surface 216 of the platform 212. Furthermore, while the "caudal" portion of the specimen has been discussed as facing the first fixed portion of the system and the "anterior" portion of the specimen has been discussed as facing the second fixed portion of the system, the present utilities encompass other portions of the specimen facing the first and second fixed portion of the system, whereupon the controller would be able to automatically superimpose graphical orientation indications into resulting images based on an assumed position of the specimen during such image generation. Furthermore, while the present disclosure discusses imparting respective sets of graphical orientation indications into or alongside resulting images, some arrangements envision that only a single graphical orientation may be superimposed into a resulting image.

In another arrangement, it is envisioned that the resulting images obtained herein (e.g., those in FIGS. 8 and 9) may be associated with, incorporated into, and/or combined with corresponding mammography images (e.g., as obtained via any appropriate picture archiving and communication system (PACS) in any appropriate manner. As an example, the computing system/controller 300 may be configured to utilize the orientation indications 1200, reference axes 1100, 1104, 1108, and/or the like to properly orient and position the obtained two- and three-dimensional images within or relative to mammography images. Additionally or alternatively, the controller may be able to utilize data from a RFID tag 1300 (see FIG. 8) previously implanted into the specimen to aid the surgeon in excising the same. In one embodiment, the computing system/controller 300 may be configured to scale the obtained two- and three-dimensional images of the specimen to the mammography images.

In another arrangement, the specimen S may be fixed or secured relative to the receiving surface 216 of the platform 212 (e.g., as well as to the at least one indicator 800) after imaging for transport to pathology or the like. This arrangement advantageous seeks to ensure that the specimen S remains correctly oriented for use by pathology and the like in conjunction with analysis of the obtained images. As an example, a lid or cover may be applied over the receiving surface 216 and that is configured to apply pressure to or compress the specimen S against the receiving surface 216 to inhibit movement of the specimen S relative to the receiving surface 216. After imaging, for instance, such cover may be applied over the specimen S and secured to the upper portion 600 of the platform 212. The upper portion 600 may then be lifted away from the lower portion 700 and transported to pathology or the like.

Figure 12:
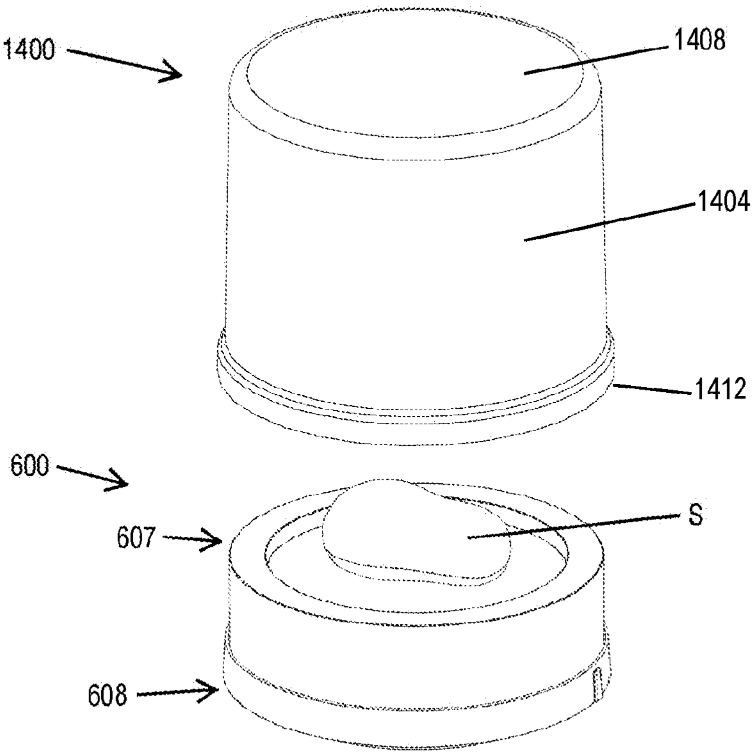
FIG. 12 is a perspective view of the receiving tray with a specimen thereon and a lid for containing the specimen, with the lid being separated from the receiving tray.
Figure 13:
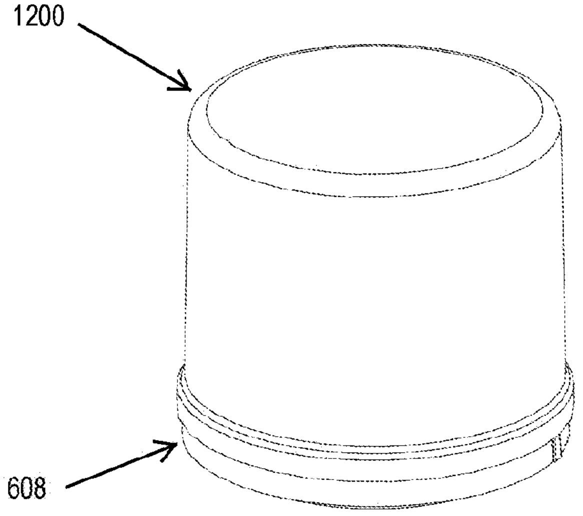
FIG. 13 is a perspective view similar to FIG. 12 but with the lid secured over the receiving tray.

In one variation, a lid may be placed over the specimen S and the upper portion 600 to protect the specimen during transport to pathology but substantially free of disturbing the specimen. In this regard, FIGS. 12-13 illustrate a lid 1400 that is placeable over the specimen S and upper portion 600 to protect the specimen S free of contacting the specimen S. For instance, the lid 1400 may generally include an outer peripheral wall 1404 that is generally configured to match the shape of the outer periphery of the upper portion 600 (e.g., cylindrical in this case), a closed first or upper end 1408 (e.g., upper wall), an open second or bottom end 1412, and an interior cavity (not labeled) within the outer peripheral wall 1404 between the upper and lower ends 1408, 1412. Upon conclusion of an imaging procedure before transport to pathology or the like, a surgeon or the like may place the closed bottom end 1412 of the lid 1400 over the specimen S and receiving surface 216 of the upper portion 600 so that the closed bottom end 1412 receives the specimen S and top portion 607 and thereafter makes contact with the bottom portion 608. Compare FIGS. 12 and 13. The lid 1400 may be retained on the upper portion 600 via a friction fit and/or in other manners (e.g., clips, spring-loaded members, etc.).

In one embodiment, a lid may be placeable over the receiving surface 216 in a manner to indicate orientations of the specimen relative to the patient's body. For instance, an upper/outer surface of the lid may have a plurality of anatomical indications thereon (e.g., caudal, cranial, lateral, etc.) and the surgeon or other operator may place the lid over the receiving surface such that such indications align with the corresponding portions of the specimen. Alternatively, the surgeon may be able to apply labeling to the lid to indicate such orientations. Additionally or alternatively, one or more pins, clips, or the like may be inserted through or attached to peripheral portions of the specimen S and into the receiving surface 216 to secure the specimen S against movement relative to the receiving surface 216.

While the disclosed utilities are primarily discussed herein in the context of imaging systems including fixed electromagnetic radiation sources and imaging detectors and a rotatable specimen receiving platform, the utilities disclosed herein are also applicable to imaging systems that include rotatable electromagnetic radiation sources and imaging detectors and fixed specimen receiving platforms.

While the disclosed system 100 has been primarily illustrated as having a single indicator 800 towards which a first particular portion of a specimen S is intended to be positioned, it is envisioned that the system 100 could have additional indicators 800 on the platform 212 and/or on other portions of the system 100 (e.g., on the cabinet 200) for conveying to a medical professional how a specimen Sis to be positioned and/or oriented over the platform 212 so that various respective portions of a specimen in an image automatically align with the graphical orientation indications imparted into or alongside the image by the computing system 300.

In some arrangements, physical or projected orientation indicators in the system may not always be needed to properly orient a specimen over the receiving surface 216 so that the orientation indications superimposed by the controller in resulting images automatically align with corresponding portions of the specimen. For instance, an operator may be instructed on a display screen concurrent with the imaging procedure to place the specimen onto the platform 212 inside the cabinet 200 with a first particular portion of the specimen (e.g., caudal) facing to the right towards the first fixed portion (e.g., sidewall 236) and a second particular portion of the specimen (e.g., anterior) facing upwardly toward a second fixed portion (e.g., top wall 246). In one characterization, the first and second fixed portions may be considered indicators.

The various two-dimensional images obtained herein need not necessarily or only include orthogonal images. That is, in some situations, two-dimensional images that are other than orthogonal may be obtained and orientation indications imparted therein based on the particular rotational position of the platform about the rotational axis when each such image was obtained.

As mentioned, embodiments disclosed herein can be implemented as one or more computer program products, i.e., one or more modules of computer program instructions encoded on a computer-readable medium for execution by, or to control the operation of, data processing apparatus (processors, cores, etc.). The computer-readable medium can be a machine-readable storage device, a machine-readable storage substrate, a memory device, a composition of matter affecting a machine-readable propagated signal, or a combination of one or more of them. In addition to hardware, code that creates an execution environment for the computer program in question may be provided, e.g., code that constitutes processor firmware, a protocol stack, a database management system, an operating system, or a combination of one or more of them.

A computer program (also known as a program, software, software application, script, or code) used to provide the functionality described herein can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

While this disclosure contains many specifics, these should not be construed as limitations on the scope of the disclosure or of what may be claimed, but rather as descriptions of features specific to particular embodiments of the disclosure. Certain features, arrangements, and the like that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

What is claimed is:

1. A method of generating images of a specimen comprising:

positioning the specimen on a receiving surface of an imaging system platform disposed within an interior chamber of an imaging cabinet, the imaging system platform being at a home position;

operating an x-ray source to emit an x-ray beam along a first axis through the specimen when the imaging system platform is in the home position and towards an x-ray imaging detector and generating at least one first image of the specimen along the first axis;

rotating the imaging system platform from the home position towards a rotational position;

operating the x-ray source to emit an x-ray beam along a second axis through the specimen when the imaging system platform is in the rotational position and towards the x-ray detector and generating at least one second image of the specimen along the second axis; and displaying at least one two-dimensional or three-dimensional specimen image based on the at least one first image and the at least one second image, wherein at least one graphical indication is automatically superimposed on the at least one two-dimensional or three-dimensional specimen image based on the known home and rotational positions of the imaging system platform.

2. The method of claim 1, wherein the at least one graphical indication includes anatomical indications comprising anterior, posterior, medial, lateral, superior, or inferior lettering or text displayed on the at least one two-dimensional or three-dimensional specimen image.

3. The method of claim 2, wherein the anatomical indicators are adjacent, but spaced, from the specimen on the displayed the at least one two-dimensional or three-dimensional specimen image.

4. The method of claim 1, wherein the at least one graphical indication includes a reference axis overlayed on the specimen on the displayed the at least one two-dimensional or three-dimensional specimen image.

5. The method of claim 1, wherein the at least one graphical indication includes anatomical indications with a corresponding reference axis on the displayed the at least one two-dimensional or three-dimensional specimen image.

6. The method of claim 5, wherein the at least one graphical indication further includes background colors in the displayed the at least one two-dimensional or three-dimensional specimen image.

7. The method of claim 1, wherein two-dimensional specimen images are displayed and include the at least one graphical indication superimposed on both the at least one first image and the at least one second image.

8. The method of claim 1, further comprising:

reconstructing a plurality of images that include the at least one first image and the at least one second image into a three-dimensional dataset; and displaying the three-dimensional specimen image that includes a manipulatable three-dimensional image and a slice image, both the manipulatable three-dimensional image and the slice image include the at least one graphical indication that is superimposed on the manipulatable three-dimensional image and the slice image.

9. The method of claim 1, wherein the home position of the imaging system platform is such that a first portion of the specimen faces a first fixed portion of the interior chamber and a different second portion of the specimen faces a different second fixed portion of the interior chamber, and wherein the positioning of the specimen on the receiving surface is aided via at least one indicator associated with the imaging cabinet, wherein the at least one indicator is radiopaque or outside a field of view of the x-ray source.

10. The method of claim 1, wherein the home position of the imaging system platform is such that a first portion of the specimen faces a first fixed portion of the interior chamber and a different second portion of the specimen faces a different second fixed portion of the interior chamber, and wherein the positioning of the specimen on the receiving surface is aided via instructions displayed on a display screen of the imaging cabinet.

11. An imaging cabinet comprising:

a housing including an interior chamber;

an x-ray source and an x-ray imaging detector positioned relative to the interior chamber;

an imaging system platform having a receiving surface disposed within the interior chamber and rotatable therein;

a display; and a controller configured to:

define a home position of the imaging system platform configured to receive a specimen on the receiving surface;

operate the x-ray source to emit an x-ray beam along a first axis through the specimen when the imaging system platform is in the home position and towards the x-ray imaging detector and generate at least one first image of the specimen along the first axis;

rotate the imaging system platform from the home position towards a rotational position;

operate the x-ray source to emit an x-ray beam along a second axis through the specimen when the imaging system platform is in the rotational position and towards the x-ray detector and generate at least one second image of the specimen along the second axis; and display at least one two-dimensional or three-dimensional specimen image based on the at least one first image and the at least one second image, wherein at least one graphical indication is automatically superimposed on the at least one two-dimensional or three-dimensional image based on the known home and rotational positions of the imaging system platform.

12. The imaging cabinet of claim 11, wherein the at least one graphical indication includes anatomical indications comprising anterior, posterior, medial, lateral, superior, or inferior lettering or text on the displayed the at least one two-dimensional or three-dimensional specimen image.

13. The imaging cabinet of claim 12, wherein the anatomical indicators are adjacent, but spaced, from the specimen on the displayed the at least one two-dimensional or three-dimensional specimen image.

14. The imaging cabinet of claim 11, wherein the at least one graphical indication includes a reference axis overlayed on the specimen on the displayed the at least one two-dimensional or three-dimensional specimen image.

15. The imaging cabinet of claim 11, wherein the at least one graphical indication includes anatomical indications with a corresponding reference axis on the displayed the at least one two-dimensional or three-dimensional specimen image.

16. The imaging cabinet of claim 15, wherein the at least one graphical indication further includes background colors in the displayed the at least one two-dimensional or three-dimensional specimen image.

17. The imaging cabinet of claim 11, wherein the imaging support platform includes at least one indicator for positioning the specimen on the receiving surface such that when the specimen is received on the receiving surface, a first portion of the specimen faces a first fixed portion of the interior chamber and a different second portion of the specimen faces a different second fixed portion of the interior chamber, the at least one indicator radiopaque or disposed outside a field of view of the x-ray source.

18. The imaging cabinet of claim 17, wherein the at least one indicator is aligned with the first fixed portion of the interior chamber.

19. The imaging cabinet of claim 11, wherein the imaging support platform includes a lower portion and an upper portion having the receiving surface, at least the receiving surface constructed from radiolucent material.

20. The imaging cabinet of claim 19, further comprising a lid removably coupled to the upper portion.

* * * * *